(12) United States Patent
McMichael

(10) Patent No.: US 11,602,280 B2
(45) Date of Patent: Mar. 14, 2023

(54) IN-SCALE FLEXIBLE DISPLAY FOR MEDICAL DEVICE POSITION GUIDANCE

(71) Applicant: Avent, Inc., Alpharetta, GA (US)

(72) Inventor: Donald McMichael, Roswell, GA (US)

(73) Assignee: Avent, Inc., Alpharetta, GA (US)

(*) Notice: Subject to any disclaimer, the term of this patent is extended or adjusted under 35 U.S.C. 154(b) by 458 days.

(21) Appl. No.: 16/377,308

(22) Filed: Apr. 8, 2019

(65) Prior Publication Data
US 2020/0315493 A1 Oct. 8, 2020

(51) Int. Cl.
A61B 5/06 (2006.01)
A61B 34/20 (2016.01)
A61B 5/00 (2006.01)
A61B 34/00 (2016.01)
A61J 15/00 (2006.01)

(52) U.S. Cl.
CPC ............. *A61B 5/062* (2013.01); *A61B 5/065* (2013.01); *A61B 5/6852* (2013.01); *A61B 5/7425* (2013.01); *A61B 34/20* (2016.02); *A61B 5/0084* (2013.01); *A61B 34/73* (2016.02); *A61B 2034/2051* (2016.02); *A61B 2034/731* (2016.02); *A61J 15/0015* (2013.01)

(58) Field of Classification Search
CPC . A61B 34/20; A61B 5/065; A61B 2034/2051; H01L 2251/5338; H01L 51/0097; G06F 1/1652; G02F 1/133305
See application file for complete search history.

(56) References Cited

U.S. PATENT DOCUMENTS

| | | |
|---|---|---|
| 4,836,214 A | 6/1989 | Sramek |
| 4,921,481 A | 5/1990 | Danis et al. |
| 6,334,064 B1 | 12/2001 | Fiddian-Green |
| 6,357,447 B1 | 3/2002 | Swanson et al. |
| 7,818,155 B2 | 10/2010 | Stuebe et al. |
| 8,147,486 B2 | 4/2012 | Honour et al. |
| 8,613,702 B2 | 12/2013 | Feer et al. |
| 8,801,601 B2 | 8/2014 | Prisco et al. |
| 8,986,230 B2 | 3/2015 | Nishtala |
| 9,179,971 B2 | 11/2015 | Kirschenman |
| 9,226,878 B2 | 1/2016 | Elia et al. |
| 9,295,395 B2 | 3/2016 | Elia et al. |
| 9,532,739 B2 | 1/2017 | Bennett-Guerrero |
| 9,610,227 B2 | 4/2017 | Elia |
| 9,642,779 B2 | 5/2017 | Elia et al. |
| 9,713,579 B2 | 7/2017 | Elia et al. |
| 9,918,907 B2 | 3/2018 | Kuhn |
| 2008/0097179 A1 | 4/2008 | Russo |
| 2008/0167607 A1 | 7/2008 | Pfeiffer et al. |
| 2008/0249467 A1 | 10/2008 | Burnett et al. |

(Continued)

FOREIGN PATENT DOCUMENTS

| | | |
|---|---|---|
| EP | 1 837 828 A2 | 9/2007 |
| WO | WO 92/17150 | 10/1992 |
| WO | WO 2006/076214 A2 | 7/2006 |

*Primary Examiner* — Jason M Ip
(74) *Attorney, Agent, or Firm* — Dority & Manning, P.A.

(57) ABSTRACT

An in-scale display device is provided. The in-scale display device includes at least one flexible electronic display screen that is configured to display at least one reference image in-scale with a subject. A medical device position guidance system including the in-scale display device and an invasive medical device system, and a method of using the medical device position guidance system, are also provided.

12 Claims, 9 Drawing Sheets

(56) References Cited

U.S. PATENT DOCUMENTS

| | | |
|---|---|---|
| 2009/0253960 A1* | 10/2009 | Takenaka ........... A61B 1/00029 |
| | | 600/118 |
| 2012/0016256 A1 | 1/2012 | Mabary et al. |
| 2012/0277619 A1 | 11/2012 | Starkebaum et al. |
| 2013/0144124 A1 | 6/2013 | Prisco et al. |
| 2013/0197357 A1 | 8/2013 | Green et al. |
| 2013/0225946 A1 | 8/2013 | Feer et al. |
| 2014/0357984 A1* | 12/2014 | Wallace ................. A61B 5/062 |
| | | 600/424 |
| 2015/0238388 A1 | 8/2015 | Kuhn |
| 2015/0282734 A1 | 10/2015 | Schweikert et al. |
| 2016/0113843 A1 | 4/2016 | Elia et al. |
| 2016/0129223 A1 | 5/2016 | Kirschenman |
| 2016/0331298 A1 | 11/2016 | Burnett et al. |
| 2017/0071502 A1 | 3/2017 | Bennett-Guerrero |
| 2017/0119329 A1 | 5/2017 | Warner et al. |
| 2017/0202750 A1 | 7/2017 | Elia |
| 2018/0078195 A1 | 3/2018 | Sutaria et al. |
| 2018/0092698 A1 | 4/2018 | Chopra et al. |
| 2018/0110440 A1 | 4/2018 | Tegg |
| 2018/0161249 A1 | 6/2018 | Elia et al. |
| 2018/0289536 A1 | 10/2018 | Burnett |
| 2019/0012944 A1* | 1/2019 | Hall ....................... A61B 1/042 |
| 2019/0259822 A1* | 8/2019 | Jeon .................... H01L 27/3262 |

* cited by examiner

IN-SCALE FLEXIBLE DISPLAY FOR MEDICAL DEVICE POSITION GUIDANCE

FIELD OF THE INVENTION

The subject matter of the present invention relates generally to a medical device position guidance system having a flexible display configured to display an in-scale reference image of an invasive medical device.

BACKGROUND

Physicians and other health care providers frequently use catheters to treat patients. The known catheters include a tube which is inserted into the human body. Certain catheters are inserted through the patient's nose or mouth for treating the gastrointestinal tract. These catheters, sometimes known as enteral catheters, typically include feeding tubes. The feeding tube lies in the stomach or intestines, and a feeding bag delivers liquid nutrient, liquid medicine or a combination of the two to the patient.

Other types of catheters are inserted into the patient's veins or arteries for treating the cardiovascular system. These intravascular catheters include, among others, the central venous catheter, peripheral venous catheter and the peripherally inserted central catheter. These catheters include a relatively small tube that passes through the patient's veins or arteries. Depending on the application, the health care providers can use these intravascular catheters to remove blood vessel blockages, place inserts into blood vessels and to provide patients with injections of medications, drugs, fluids, nutrients, or blood products over a period of time, sometimes several weeks or more.

When using these known enteral and intravascular catheters, it is important to place the end of the catheter at the proper placement within the human body. Erroneous placement of the catheter tip may injure or harm the patient. For example, if the health care provider erroneously places an enteral catheter into the patient's lungs, liquid may be introduced into the lungs with harmful results.

If the health care provider erroneously places an intravascular catheter into the wrong blood vessel of the cardiovascular system, the patient may experience infection, injury or a harmful blockage.

It is also prudent to check that the exit aperture of the feeding tube (typically located at the distal end/tip of the tube) remains in its desired location over the period of treatment, e.g., feeding. Protocols that address this requirement in enteral feeding tubes include frequent monitoring for the appropriate pH of fluids extracted from the feeding tube when not carrying nutritional liquids and careful patient monitoring to ensure nutritional uptake is as expected.

One existing catheter locating means involves using an electromagnetic coil positioned inside the catheter and an electromagnetic coil locating receiver outside of the patient's body to approximate and display the catheter position. However, these systems also have several disadvantages. For example, there can be discrepancies between the size and placement of the catheter tube shown on the display and the actual size and placement of the catheter tube. These discrepancies can lead to users misinterpreting the displayed information related to the placement of the catheter tube within the subject.

For example, the coil locating receiver is a large device that must rest in a precise location outside the patient's body and does not permit for adjustments due to a patient's anatomical size or shape. Additionally, these existing systems can only display the coil location over a reference image of a non-subject (i.e., a generic patient) body without reference to the subject's particular anatomy. Therefore, while health care providers can estimate the positioning of the catheter using the electromagnetic coil and coil locating receiver, they cannot estimate or view the specific patient's anatomy.

Consequently, there is a need for an in-scale display for a medical device position guidance system. In particular, an in-scale display that rests on a subject and displays the placement of a medical device in-scale with the subject would also be useful.

SUMMARY

The present invention is directed to a display device including at least one flexible electronic display screen, at least one signal receiver configured to detect a signal generated by a signal generator, a processor, and a memory device. The memory device stores instructions which, when executed by the processor, cause the processor to (i) detect the signal generated by the signal generator, (ii) determine the distance between the at least one signal receiver and the signal generator, and (iii) cause the display device to display at least one reference image of the location of the signal generator on the at least one flexible electronic display screen in-scale with the subject's body when the signal generator is positioned below the display device.

In one particular embodiment, the display device can further include a substrate having an attachment device configured to secure the display device to the subject. Moreover, the attachment device can be configured to secure the display device to a garment worn by the subject. Further, the substrate can include a flexible wrap. Moreover, the flexible wrap can be configured to be adjustable in size based on a size of the subject's body.

In another embodiment, the at least one flexible electronic display screen can include a first flexible electronic display screen and a second flexible electronic display screen. Moreover, the first flexible electronic display screen and the second flexible electronic display screen can be integrated into a substrate having an attachment device configured to secure the display device to the subject's body. Further, the second flexible electronic display screen can be configured to be positioned generally perpendicular to the first flexible electronic display screen when the attachment device is secured to the subject's body. Moreover, the first flexible electronic display can be configured to be positioned on an anterior or posterior surface of the subject's body and the second flexible electronic display can be configured to be positioned on a lateral surface of the subject's body. In addition, the substrate can include a flexible wrap. Moreover, the flexible wrap can include an adjustable section positioned between the first flexible electronic display and the second flexible electronic display. In one embodiment, first flexible electronic display screen can be configured to display movement of the signal generator in the superior/inferior and lateral/medial directions of the subject's body. In an embodiment, the second flexible electronic display screen can be configured to display movement of the signal generator in the superior/inferior and dorsal/ventral directions of the subject's body.

In an additional embodiment, the at least one flexible electronic display can include at least one flexible LED mat.

In yet another embodiment, the signal receiver can be an electromagnetic receiver, further wherein the signal generator is an electromagnetic field generator.

The present invention is further directed to a medical device position guidance system including an invasive medical device assembly and a display device. The display device is positionable over a surface of a subject. The invasive medical device assembly includes a signal generator and an invasive medical device configured to support the signal generator, the invasive medical device having an end portion configured to be inserted into the subject. The display device includes at least one flexible electronic display screen, at least one signal receiver configured to detect a signal generated by the signal generator generator of the invasive medical device assembly; a processor; and a memory device storing instructions. When the instructions are executed by the processor, they cause the processor to (i) detect the signal emitted by the signal generator, (ii) determine the distance between the at least one signal receiver and the signal generator, and (iii) cause the display device to display at least one reference image of the location of the signal generator on the at least one flexible electronic display screen in-scale with the subject's body when the invasive medical device assembly is positioned below the display device.

In one particular embodiment, the at least one flexible electronic display screen can include a first flexible electronic display screen and a second flexible electronic display screen. Moreover, the first flexible electronic display can be configured to be positioned on an anterior or posterior surface of the subject's body and the second flexible electronic display can be configured to be positioned on a lateral surface of the subject's body. In addition, the first flexible electronic display screen can be configured to display movement of the signal generator in the superior/inferior and lateral/medial directions of the subject's body, and the second flexible electronic display screen can be configured to display movement of the signal generator in the superior/inferior and dorsal/ventral directions of the subject's body.

The present invention is further directed to a method of guiding the positioning of an invasive medical device. The method includes a step of providing a medical device position guidance system. The system includes an invasive medical device assembly including a signal generator and an invasive medical device configured to support the signal generator, the invasive medical device having an end portion configured to be inserted into the subject. The system further includes a display device having at least one flexible electronic display screen; at least one signal receiver configured to detect a signal generated by the signal generator of the invasive medical device assembly; a processor; and a memory device storing instructions which, when executed by the processor, cause the processor to (i) detect the signal generated by the signal generator, (ii) determine the distance between the at least one signal receiver and the signal generator, and (iii) cause the display device to display at least one reference image of the location of the signal generator on the at least one flexible electronic display screen in-scale with the subject's body when the invasive medical device assembly is positioned below the display device. The method includes further steps of: positioning the display device on a surface of the subject's body in a predetermined arrangement such that the at least one signal receiver is in a predetermined position; determining the position of the signal generator relative to the at least one signal receiver; and displaying the position of the signal generator in-scale on the at least one flexible display when the signal generator passes an area of the subject covered by the display device.

In one particular embodiment of the method the at least one flexible electronic display screen includes a first flexible electronic display screen configured to display movement of the signal generator in-scale in the superior/inferior and lateral/medial directions of the subject's body and a second flexible electronic display screen configured to display movement of the signal generator in-scale in the superior/inferior and dorsal/ventral directions of the subject's body.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
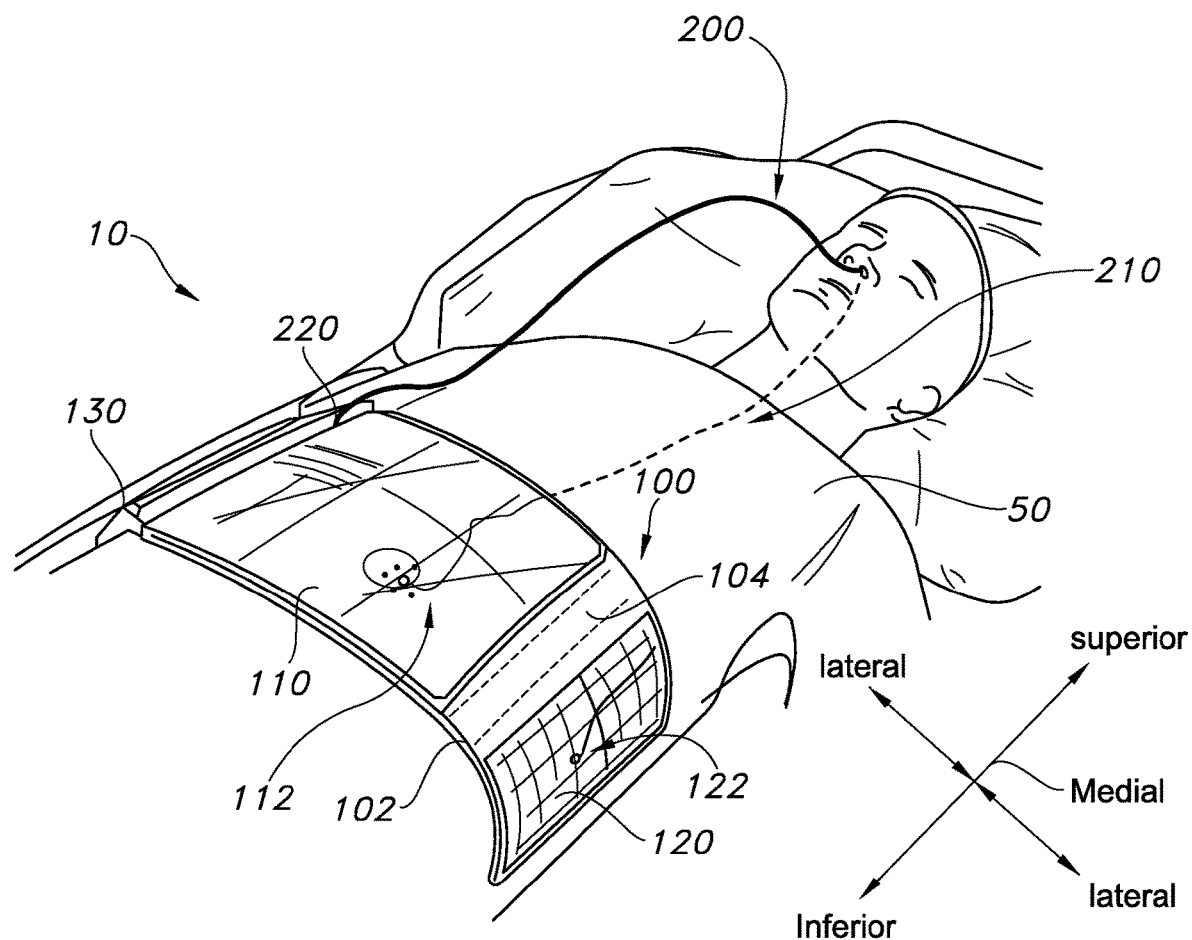
FIG. 1 illustrates a perspective view of a display device used in a medical device position guidance system according to one particular embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment.

As used herein, the term "in-scale" indicates an article or image that is in proportion to its surroundings, with all parts the right size in relation to each other.

Generally speaking, the present invention is directed to a display device for a medical device position guidance system. The display device includes at least one flexible electronic display screen. The display device additionally includes at least one signal receiver configured to detect a signal generated by a signal generator; a processor; and a memory device storing instructions. When the instructions are executed by the processor, they cause the processor to (i) detect the signal generated by the signal generator, (ii) determine the distance between the at least one signal receiver and the signal generator, and (iii) cause the display device to display at least one reference image of the location of the signal generator on the at least one flexible electronic display screen in-scale with the subject's body when the signal generator is positioned below the display device. A medical device position guidance system including the display device and a method for the use of the system during placement of a medical device inside a body are also provided. The at least one reference image is in-scale with the signal generator. Because of the specific components of the display device, medical device position guidance system, and their methods of use, the present inventor has found that the placement of a medical device within a subject's body can be more accurately graphically represented in-scale with the anatomy of the body to improve the ease of placement of the medical device. The specific features of the in-scale display device of the present invention may be better understood with reference to FIGS. 1-7.

Figure 2:
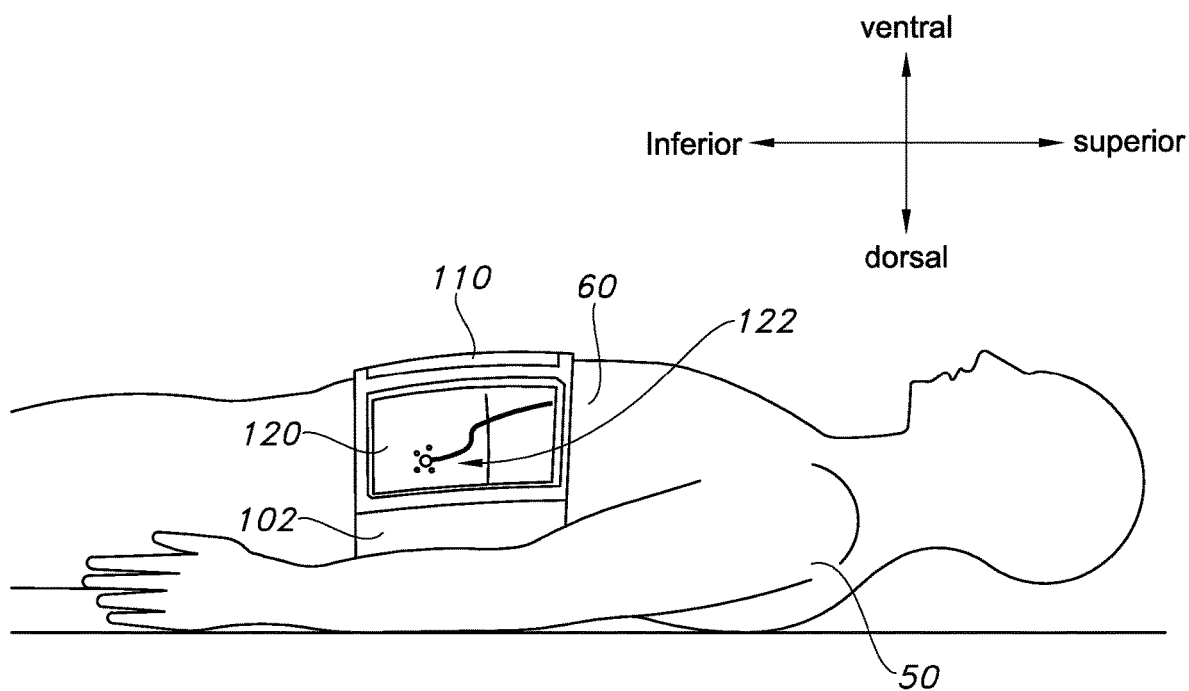
FIG. 2 illustrates a side view of the display device in use according to FIG. 1.
Figure 3:
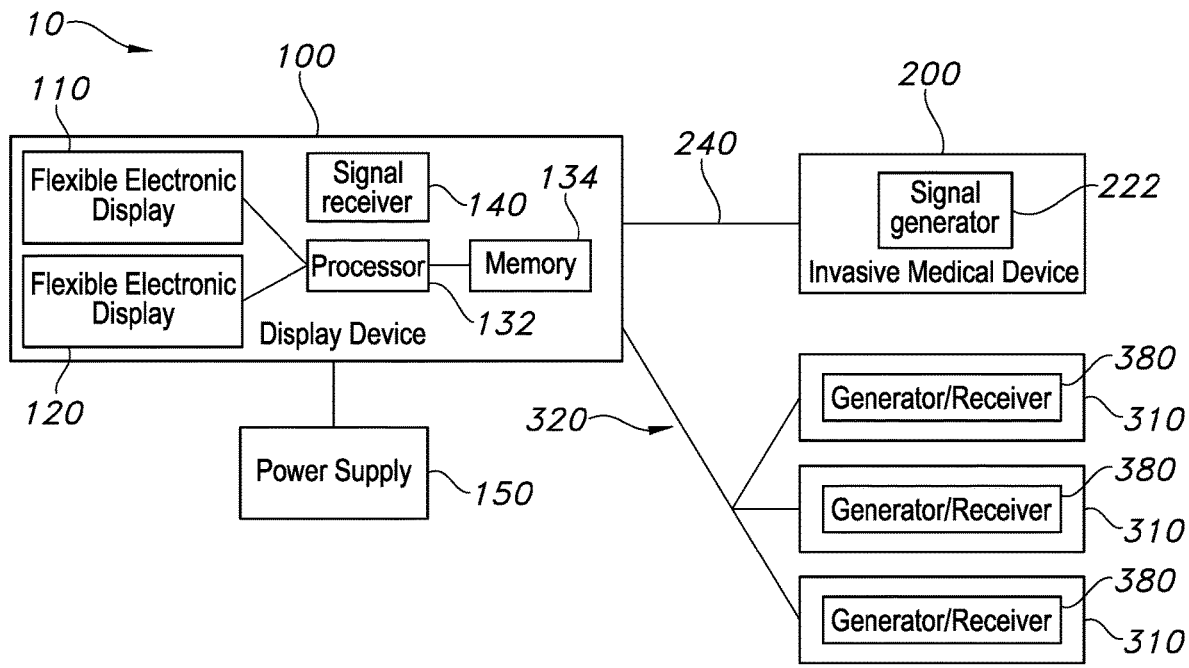
FIG. 3 illustrates a block diagram of one embodiment of a medical device position guidance system according to the present invention.

Referring now to FIGS. 1-3, one embodiment of an in-scale display device 100 for a medical device position guidance system 10 includes: a first flexible electronic display screen 110 and a control unit 130 attached to a substrate 102. The in-scale display device 100 can also include a second flexible electronic display screen 120. As shown in FIG. 3, the control unit 130 can include a processor 132 and a memory unit 134. The in-scale display device 100 additionally includes a signal receiver 140, e.g., an electromagnetic receiver, that is configured to detect a signal (e.g., an electromagnetic field) and send signals related to the received signal to the processor 132. The signal receiver 140 can be located within the control unit 130 or otherwise incorporated into the in-scale display device 100. For example, in some embodiments (not shown), the signal receiver 140 can have a separate housing that is releasably attached to the in-scale display device 100.

The substrate 102 is configured to support the display device 100 and hold it in place relative to the body of the subject 50. For example, the substrate 102 can be a mat, a sheet, a film, a laminate, or any other suitable structure for supporting the display device 100. In one embodiment, the substrate 102 can form a band or wrap configured to be placed around at least a portion of the subject's body 50. For example, as shown in FIGS. 1-2, the substrate 102 can wrap over and around the trunk 60, e.g., thorax or abdomen, of the subject 50. The substrate can be made from any suitable flexible material, such as but not limited to flexible polyvinyl chloride (PVC), acrylic, or polycarbonate. In another embodiment, the substrate can be a woven material or fabric. The substrate can have a thickness in a range from about 1/16 inch (1.5 mm) to about 1 inch (25.4 mm), or any range or value therebetween, such as from about 3/32 inch (2.4 mm) to about one-half inch (12.7 mm), for example from about 1/8 inch (3.2 mm) to about one-quarter inch (6.4 mm). Optionally, the substrate 102 can include an attachment device (not shown) that is configured to secure the wrap 102 around the subject's body 50. For example, the attachment device can include one or more cooperative hook and loop fasteners, clips, buttons, zippers, releasable adhesives, or any other suitable fastener to affix the wrap 102 around the subject 50. The attachment device can be particularly useful in embodiments when the substrate 102 is in the form of a wrap configured to wrap around or encircle a portion of the subject's body 50. Additionally or alternatively, the substrate 102 can include a fixation device (not shown) that is configured to affix the substrate 102 to the subject's body 50 or garment. For example, the fixation device can include one or more releasable adhesives, clips, magnets, or any other means for affixing the substrate 102 to a subject's body 50 or garment. The fixation device can be particularly useful in embodiments in which the substrate 102 is configured to rest on the subject's body 50 without wrapping or encircling the subject's body 50.

In one embodiment, as shown in FIGS. 1-2, the first flexible electronic display 110 can be positioned on a top surface of the substrate 102 and configured to lay on a top surface of the subject 50, such as on the abdomen of the subject 50. The second flexible electronic display 120 can be positioned on a top surface of the substrate 102 and configured to lay on a lateral surface of the subject 50, such as on a lateral side of the patient's abdomen as shown in FIGS. 1-2. Thus, as shown in FIGS. 1-2, the second flexible electronic display screen can be configured to be positioned in a plane generally perpendicular to the first flexible electronic display screen when the substrate 102 is secured around the subject's abdomen. In this embodiment, the first flexible electronic display 110 can be configured to display movement of the signal generator in the superior/inferior and lateral/medial directions of the subject's body 50, and the second flexible electronic display 120 can be configured to display movement of the signal generator in the superior/inferior and dorsal/ventral directions of the subject's body 50. Although FIGS. 1-2 illustrate the second flexible electronic display 120 on a left side of the subject's body 50, it is contemplated that the second flexible electronic display 120 could be positioned on either the left side or the right side of the subject's body 50 based on the clinician's or user's needs during use of the flexible display device 100. In one embodiment, the first flexible electronic display 110 and the second flexible electronic display 120 can be modularly attached to the substrate 102 such that the first flexible electronic display 110 and the second flexible electronic display 120

In some embodiments, the substrate 102 can include an adjustable section 104. The adjustable section 104 can adjust the size of the substrate 102 to fit the size of a particular subject 50. For example, as shown in FIGS. 1-2, the adjustable section 104 can be positioned between the first flexible electronic display 110 and the second flexible electronic display 120 so that the distance between the first flexible electronic display 110 and the second flexible electronic display 120 can be expanded or contracted. In one embodiment, the adjustable section 104 can include a portion of the substrate 102 having accordion-like folds that can be expanded or contracted. In another embodiment, the adjustable section 104 can include an elastic material configured to stretch to expand to a particular subject's size. In other embodiments, the adjustable section 104 can include cooperative hook and loop fasteners, zippers, buttons, or any other suitable mechanism to increase or decrease the length of the substrate 102.

The first flexible electronic display 110 and the second flexible electronic display 120 can each be formed from a panel of flexible light emitting diodes (LED), such as organic light emitting diodes (OLED), in a multi-pixel matrix display. Each display can generally include an OLED display forming a transparent plastic flexible membrane with the organic diode elements embedded therein. No backlighting is required, as the LED elements can generate radiated light as opposed to liquid crystal display (LCD) elements that have been used in alternative flexible displays. Specifically, the OLED display emits light due to the electroluminescence of thin films of organic semiconductors. The thin film of organic semiconductor can be situated between two electrodes, a cathode and an anode, typically at least one of which is transparent. The thin films of organic semiconductors can have a thickness in a range from about 10 nm to about 200 nm, or any range or value therebetween, such as from about 50 nm to about 100 nm. The transparent plastic flexible membrane can be made of polyethylene terephthalate (PET) or any other suitable flexible plastic. Thus, the flexible electronic displays can be both bendable and lightweight. In other embodiments, the first electronic display 110 and the second electronic display 120 can be any suitable display mechanism including, but not limited to, liquid crystal displays (LCD) or plasma screens.

Figure 4:
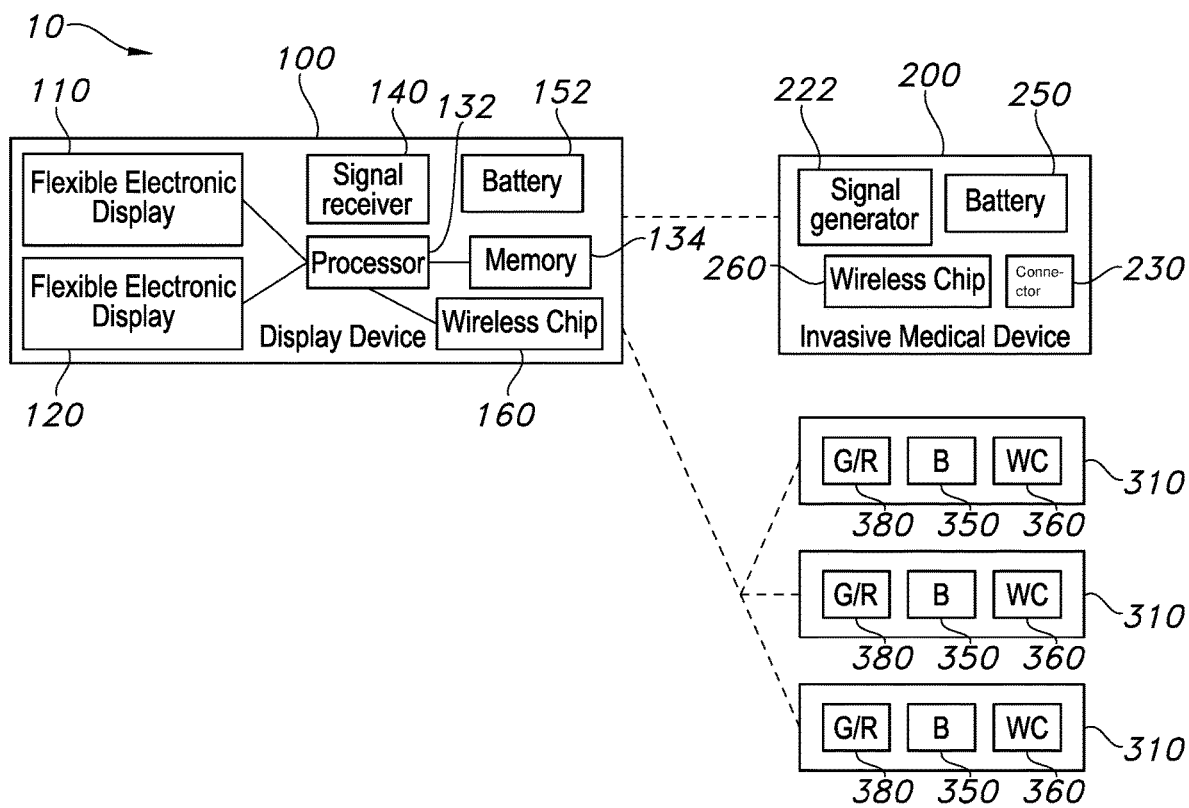
FIG. 4 illustrates a block diagram of another embodiment of a medical device position guidance system according to the present invention.

As shown in FIGS. 3-4, the display device 100 can additionally include a control unit 130. The control unit 130 can include a processor 132 and a memory unit 134. The memory unit 134 can store algorithms which, when executed, instruct the processor 132 to display at least on image 122 on at least one of the flexible electronic displays 110 and 120. The first flexible electronic display 110 and the second flexible electronic display 120 can share common driver circuits and be connected to the processor 132. The display device 100 can include a power supply 150. The power supply 150 can be contained within the control unit 130, such as a battery 152 shown in FIG. 4, or can be external to the display device 100, as shown in FIG. 3.

As shown in FIGS. 3-4, the display device 100 can also include a signal receiver 140 that is configured to detect a signal emitted by a signal generator. For example, the signal receiver 140 can be an electromagnetic receiver, for example, in the form of one or more coils of wire(s). The coil(s) can be operable to receive an induced current in response to a magnetic field generated by an electromagnetic field generator 222 when the magnetic field is directed toward and reaches the coil(s). It should be appreciated that the coil(s) of the electromagnetic receiver 140 can be any suitable structure or structures capable of receiving a current in response to a generated magnetic field. The electromagnetic receiver 140 is in communication with the processor 132 of the display device 100 to send information regarding the position and orientation of the electromagnetic field generator 222 relative to the electromagnetic receiver 140. The information regarding the position and orientation of the electromagnetic field generator 222 relative to the signal receiver 140 can be obtained by sensing the voltage of the induced current in the coil(s) and obtaining the drive signals used to create the electromagnetic field by the electromagnetic field generator 222, to assess the distance between the receiver 140 and the generator. In another embodiment, the signal receiver 140 can detect the strength of a signal on a defined frequency that is generated by the signal generator 222. The strength of the detected signal on the defined frequency can be used to determine the distance between the signal receiver 140 and the field generator 222.

The memory device 134 can store image processing algorithms which, when executed by the processor 132, cause the processor 132 to generate at least one reference image 112 on at least one of the flexible electronic displays 110 and 120 relating to the position and orientation of the electromagnetic field generator 222 relative to the electromagnetic receiver 140. The at least one reference image 112 can be displayed in-scale with the anatomy of the subject 50. The flexible electronic displays 110 and 120 can additionally display anatomical landmarks of the subject's body 50, such as bony landmarks, for example a display of the xiphoid process on the first flexible electronic display 110 when the first flexible electronic display 110 is disposed on a top surface of the subject's body 50 overlying the xiphoid process, as shown in FIG. 1.

As shown in FIGS. 3-4, the in-scale display device 100 can be part of a medical device position guidance system 10. The medical device position guidance system 10 can include an invasive medical device assembly 200, shown in FIG. 5, having an invasive medical device 210 with a signal generator system 220 (e.g., an electromagnetic field generator system), and a plurality of non-invasive external detector devices 310 electronically coupled to the processor 132 by a wire, cable, signal data connection, signal carrier or wireless connection, e.g. cable 320 shown in FIG. 1. The invasive medical device assembly 200 can be operatively connected to the display device 100 by a wired connection, shown in FIG. 3 with cable 240, or a wireless connection, shown in FIG. 4. The signal generator system 220 is configured to be disposed within the invasive medical device 210 such that the signal generator system 220 can be used to detect a position and/or orientation of the invasive medical device 210 within the subject's body 50. Each of the plurality of external detector devices 310 are configured to be positioned in a distributed arrangement on a surface of a subject 50 which is a mammal, such as a human. Although the illustrated example depicts a human, it should be appreciated that medical device position guidance system 100 could be used with any mammals such as domestic animals.

In general, and referring to FIGS. 5 and 6A-C, the plurality of noninvasive external detector devices 310 each includes a housing 312 which supports a signal generator/receiver 380 operably coupled to the processor 132, where the processor 132 is coupled to a memory device 134. According to the embodiment, the medical device position guidance system 10 is operable to provide audiovisual information about the shape, size, and orientation of a subject's anatomy through a wired or wireless connection between the plurality of external detector devices 310 and the in-scale display device 100. The medical device position guidance system 10 can be further operable to provide audiovisual information about the position and orientation of the invasive medical device 200 relative to the plurality of external detector devices 310, the position of the in-scale display device 100 relative to the subject 50, and the subject's detected anatomy, through a wired or wireless connection between the plurality of external detector devices 310, the invasive medical device 200, and the in-scale display device 100.

Figure 5:
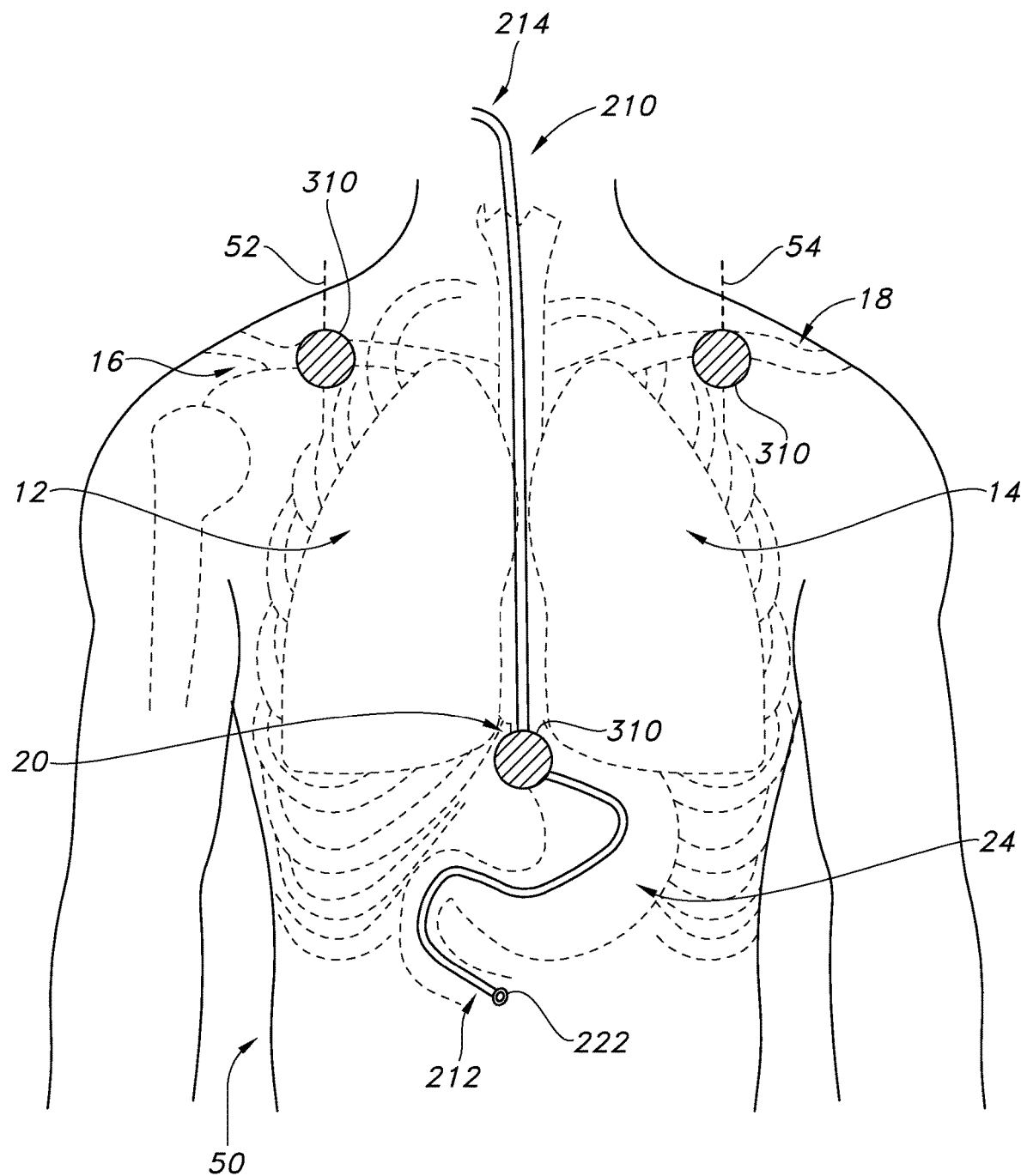
FIG. 5 illustrates a predetermined arrangement of detector devices on anatomical landmarks of a human body according to one particular embodiment of the present invention.
Figure 6A:
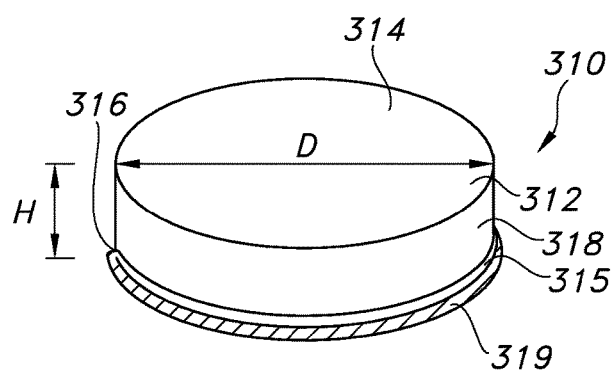
FIG. 6A illustrates a perspective view of an external detector device of the medical device position guidance system of FIG. 3.

As illustrated in FIGS. 5 and 6A-C, each of the external detector devices 310 includes a housing 312 surrounding a signal generator and/or receiver 380. The housing 312 can include an upper surface 314, a lower surface 316, and at least one side surface 318 extending from the upper surface to the lower surface. For example, as shown in FIG. 6A, the upper surface 314 and the lower surface 316 can be circular or oval in shape and have a continuous side surface 318 extending therebetween, forming a generally cylindrical-shaped housing 312. In another embodiment (not shown), the upper surface 314 and the lower surface 316 can be rectangular in shape and can have four side surfaces 318 extending therebetween corresponding to each of the sides of the rectangle. However, the external shape of the housing 312 of each external detector device 310 is of little consequence to the way in which the actual signal generator and/or receiver 380 works. As such, the housing 312 can have any other suitable external shape based on a particular application of the medical device position guidance system 100.

The housing 312 of each external detector device 110 can have a footprint (i.e., shape and size of the lower surface 316) that is generally comparable to standard electrocardiogram leads. For example, the housing 312 can have a diameter D extending across the widest portion of the upper surface 314 or lower surface 116 that is in a range from about 0.5 inches (1.25 cm) to about 5 inches (13 cm), or any value or range therebetween, such as from about 1 inch (2.5 cm) to about 3 inches (7.6 cm), for example from about 1.5 inches (3.8 cm) to about 2.5 inches (6.4 cm). The at least one side surface 318 of the housing 312 can have a height H in a range from about 0.25 inches (0.63 cm) to about 2 inches (5.1 cm), or any value or range therebetween, such as from 0.3 inches (0.76 cm) to about 1 inch (2.5 cm), for example about 0.5 inches (1.25 cm). In addition, each of the external detector devices 310 can be lightweight.

Figure 6B:
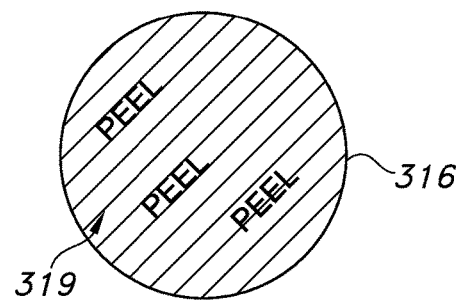
FIGS. 6B-C illustrate bottom view of the housing of FIG. 6A.
Figure 6C:
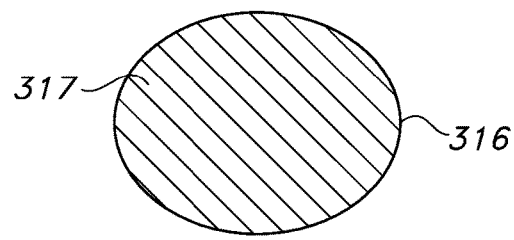

As shown in FIGS. 6A-C, each external detector device 310 can further include a fixation mechanism 315 that is configured to affix the external detector device 310 to the subject. In a preferred embodiment, the external detector device 310 can be directly affixed to the subject's body 10 by the fixation mechanism 315 so that the external detector device 310 maintains a fixed reference point in relation to the subject 50. Thus, when the subject 50 moves, the external detector device 310 moves with the subject 50 to maintain a static frame of reference with respect to the particular patient. The fixation mechanism 315 can be positioned on the lower surface 316 of the external detector device housing 312. For example, the fixation mechanism 315 can include an adhesive material 317 that is configured to affix the external detector device 310 to the skin of the subject, a patch on the subject's body, or a garment worn by the subject. The adhesive material 317 can be an adhesive substrate that can be adhesive on both sides such that it adheres to the lower surface 316 of the housing 312 on one side and to a subject's body or garment on the other side. When the fixation mechanism 315 is adhesive material 317 adhered to the lower surface 318 of the housing 312, the external detector device 310 can additionally include a peelable protective sheet 319 covering the entire adhesive material 317. The peelable protective sheet 319 can be removed prior to affixing the adhesive 317 to the subject 50 or the subject's garment. Optionally, a used adhesive substrate 317 can be removed from the housing 312 and discarded, and a new adhesive substrate 317 can be applied. Alternatively, the adhesive material 317 can be any suitable adhesive arrangement which is capable of releasably adhering the housing 312 to the subject's skin or garment. In other embodiments, the fixation mechanism 315 can include a clip, pin, magnet, hook and loop system, or any other suitable means for affixing the external detector device 310 to a subject's body or garment. By using a fixation mechanism 315 on each external detector device 310 that can affix the external detector device 310 to the subject's body or garment, the frame of reference of each external detector device 310 can remain stationary with the subject's body. Thus, the likelihood of positional errors when using the medical device position guidance system 100 can be reduced as compared to other guidance systems because there can be fewer complications arising due to movement of the subject's body.

As shown in FIG. 5, the plurality of external detector devices 310 are configured to be positioned on the external anatomy of a subject 50 in a predetermined arrangement. The predetermined arrangement of the external detector devices 310 can be specific to a particular medical device being positioned in the subject 50. The predetermined arrangement can include multiple predetermined external fixation points on the subject's external anatomy, where each of the predetermined external fixation points are distributed or separated from each other as shown in FIG. 5. The predetermined external fixation points can be based on well-known external anatomical landmarks. In some embodiments, the well-known external anatomical landmarks can be bony landmarks, as the bony landmarks can be located visually or palpated on subjects of any shape or size regardless of physical presentation of the subject, such as the presence of adipose tissue, edema, or other tissues. Having the external detector devices 310 positioned on known anatomical landmarks on the subject's body 50 provides a known anatomical frame of reference which can enable anthropometric data to be applied in order to approximate three-dimensional locations and sizes of internal anatomical structures.

For example, as illustrated in FIG. 5, when the medical device position guidance system 100 is used to determine a subject's upper anatomy such as for inserting an enteral catheter (feeding tube), three external detector devices 310 can be positioned on the subject 50. For instance, one device 310 can be placed at a right upper landmark, such as the right midclavicular line 52, one device 310 can be placed at a left upper landmark, such as the left midclavicular line 54, and one device 310 can be placed at a central landmark, such as the xiphoid process 20. As illustrated in FIG. 5, the xiphoid process 20 is the cartilaginous section at the lower end of the sternum 30 which is generally positioned along the mid-sagittal line 50 and which is not attached to any ribs 32 and is gradually ossified in adult humans. The right and left midclavicular lines 52 and 54 are each imaginary lines which are generally parallel to the mid-sagittal line 50 and pass downwards over the trunk of the human body 10 through the midpoint of the right and left clavicle bones 16 and 18, respectively. However, the midclavicular lines 52 and 54 and the xyphoid process 20 are not the only landmarks that could be used for this purpose. There may be other points of the body to which the predetermined arrangement of the plurality of external detector devices 310 could be reliably co-located or located with a predetermined offset for use in a reliable position guidance system.

As illustrated in FIGS. 3-4, each external detector device 310 includes a signal generator and/or receiver 380. In one embodiment, each external detector device may include an electromagnetic field generator formed through a plurality of coils of wire(s). The signal generator and/or receiver can receive electrical energy through a wired connection to power supply 150, as shown in FIG. 3, or can be a battery 350 within the external detector device 310 as shown in FIG. 4. When the power source sends electrical current to the signal generator 80, the signal generator 380 can transmit a signal or electromagnetic field capable of being detected by an electromagnetic receiver. Although coils are disclosed as one example of a signal generator, it should be appreciated that the signal generator can include any suitable mechanism or device which generates or produces a detectable signal such as radiofrequency generation, magnetic energy or a magnetic field, such as a permanent magnet, resistive magnet, or superconducting magnet. The signal generator/receiver 380 of each external detector device 310 can additionally or alternatively include a signal receiver that can detect an electromagnetic field or signal generated by a signal generator, such as the signal generators of the other external detector devices 310. The signal receivers can each include at least one receiver coil, such as three receiver coils, that are operable to receive an induced current and detect the induced voltage in response to a magnetic field generated by a signal generator when a signal, such as a magnetic field or defined frequency, is directed toward and reaches the receiver coil(s). It should be appreciated that the receiver may be any suitable structure capable of receiving a signal, such as an induced current in response to a generated magnetic field, or detecting the strength of a signal at a defined frequency. In some embodiments, each of the plurality of external detector devices 310 can include both signal generator and a signal receiver as part of the emitter/receiver 380. Additionally, there can be shielding within the emitter/receiver 380 to shield between the generator and the receiver. The shielding can prevent signal interference. For example, the shielding can be a barrier be made of conductive or magnetic materials.

In one embodiment, each external detector device 310 can be electrically connected to the display device 100 via a wire, cable, or other connection 320 to receive power from the display device 100 and to communicate with the processor 132. Alternatively, each external detector device 310 can have a wireless configuration including a battery 350 that provides a voltage to the signal generator/receiver 380 and a wireless communication chip 360 configured to communicate with the processor 132. Optionally, the wireless communication chip 360 can include a processor (not shown). The wireless communication chip 360 can be any suitable form of wireless communication capable of sending and receiving digital signals from the processor 132 of the display device 100.

When the plurality of external detector devices 310 are positioned in the predetermined arrangement on the subject 50 based on predetermined external landmarks, the locations of the landmarks can provide adequate separation of the external detector devices 310 on the subject to enable each of the external detector devices 310 to interrogate each other, i.e., for the signal generators to generate a signal and for the signal receivers to detect the signals generated by the respective signal generators of the other external detector devices 310.

Figure 7:
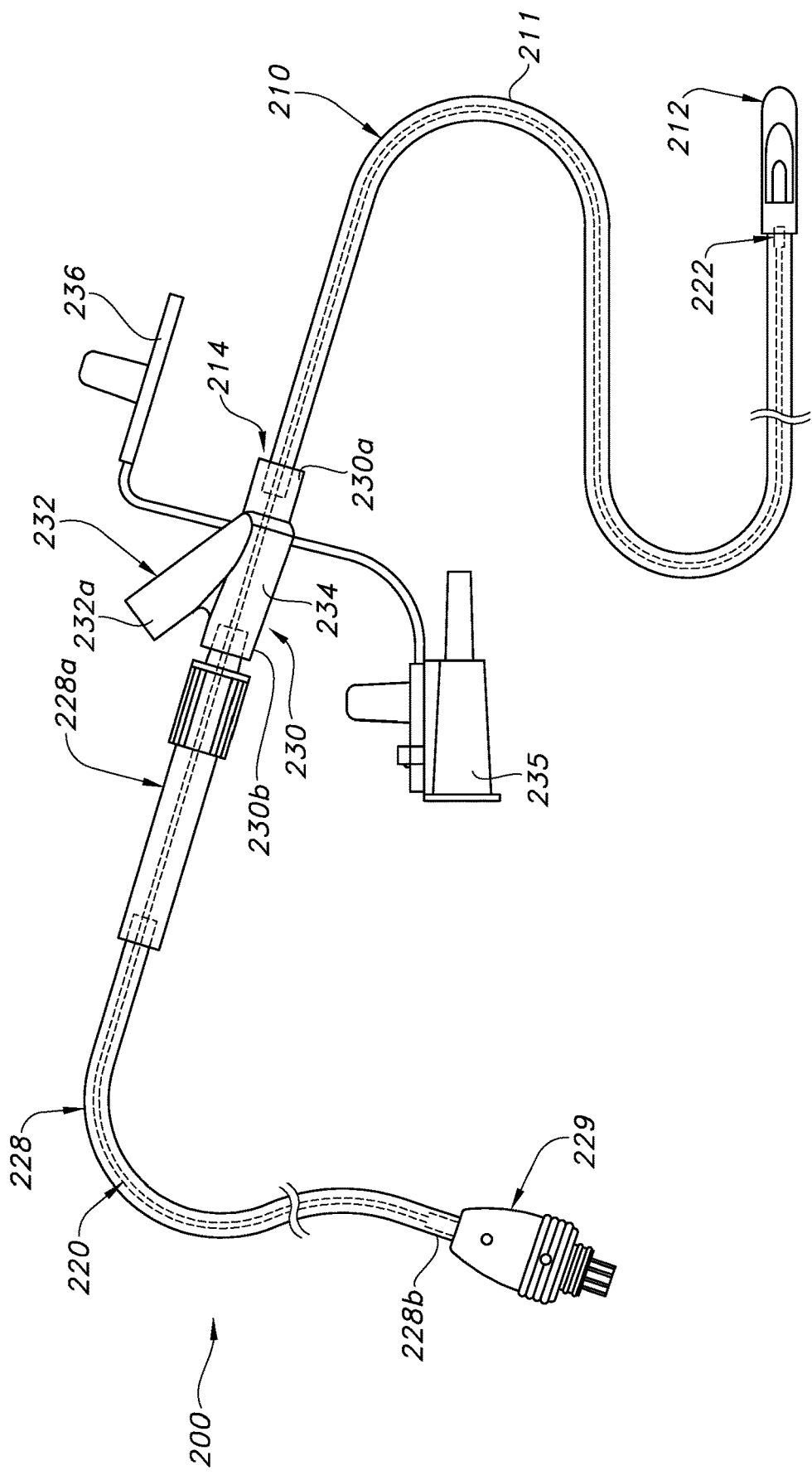
FIG. 7 illustrates a perspective view of an invasive medical device assembly of the medical device position guidance system of FIG. 3.
Figure 8:
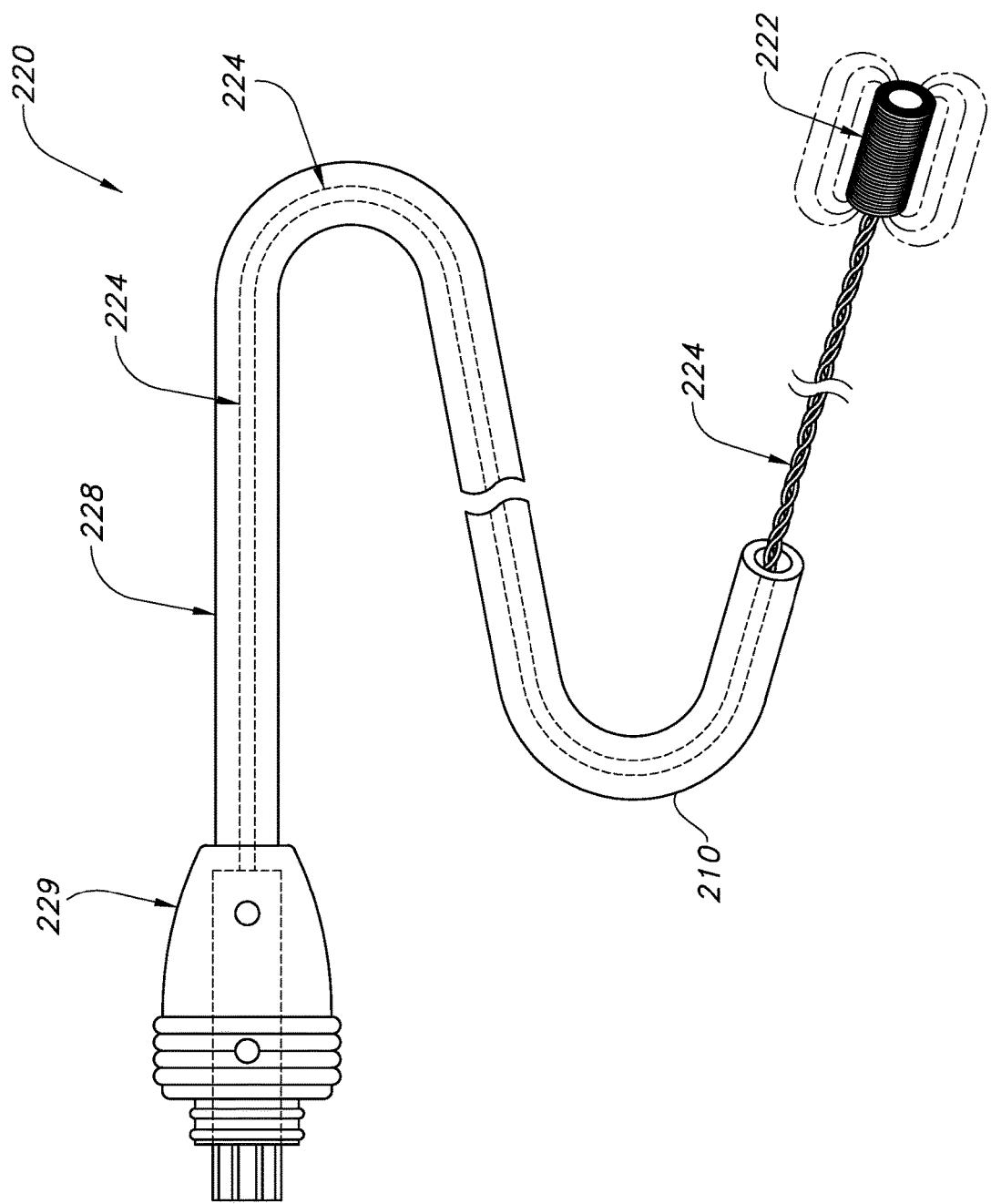
FIG. 8 illustrates a perspective view an electromagnetic field generator system of the invasive medical device assembly of FIG. 7.
Figure 9:
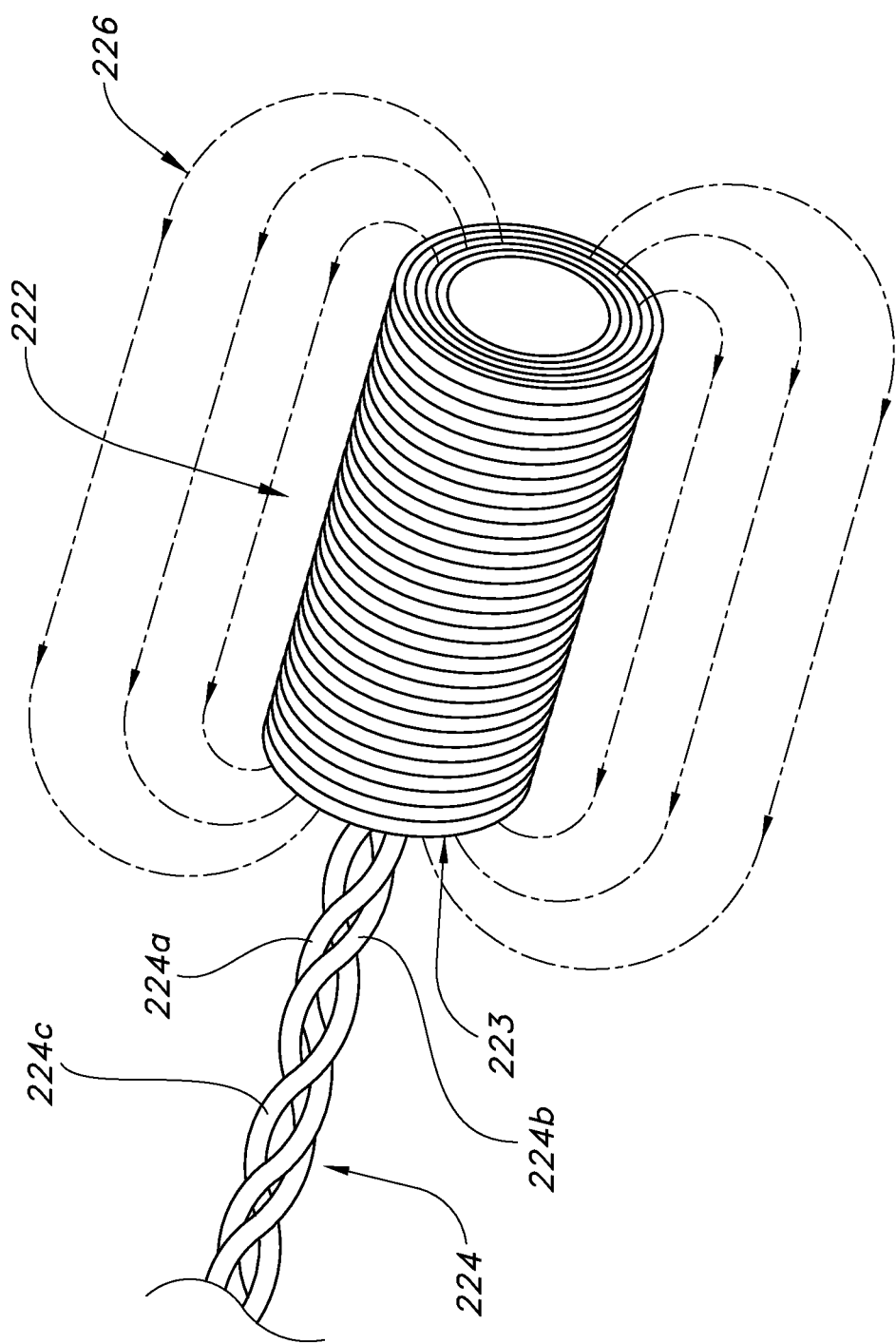
FIG. 9 illustrates an electromagnetic field generator of the embodiment of FIG. 8.
Figure 10:
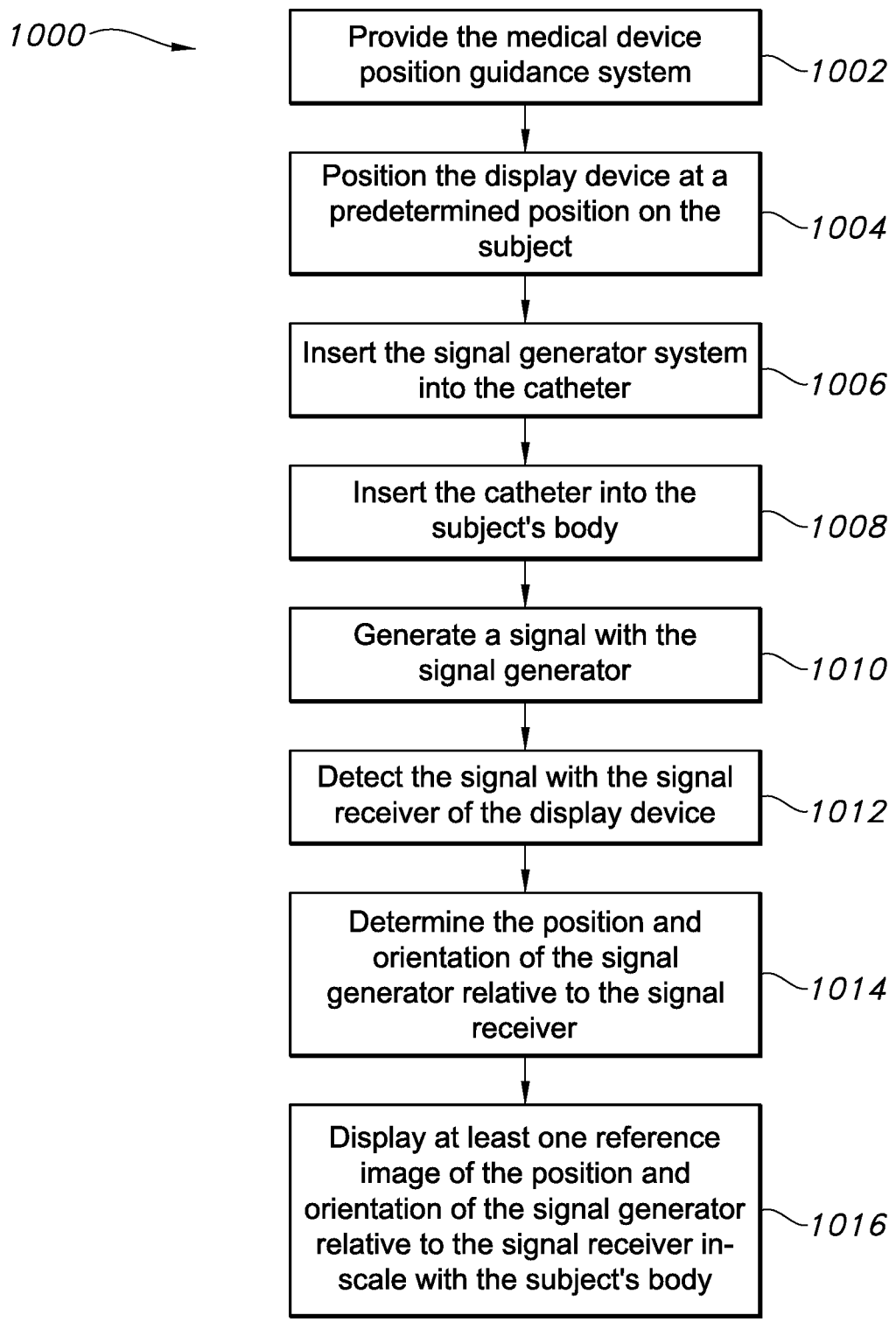
FIG. 10 illustrates a method of using the medical device position guidance system of FIG. 3.

As illustrated in FIGS. 1 and 7, the invasive medical device 210 can be a catheter, such as an enteral feeding tube 210. The enteral feeding tube 210 extends from a distal end 212 to a proximal end 214 and can be connected to a distal end 230a of a connector 230 at the proximal end 214. The invasive medical device assembly 200 can additionally include a tubing assembly 228 configured to house at least a portion of the signal generator system 220. A distal end 228a of the tubing assembly 228 can connect to a proximal end 230b of the connector 230. For example, as shown in FIG. 5, the distal end 230a and proximal end 230b of the connector 230 can extend along a longitudinal axis with a lumen 234 extending therebetween. Both the distal end 230a and proximal end 230b of the connector 230 can contain openings in communication with the lumen 234 and configured to receive the feeding tube 210 and the tubing assembly 228, respectively. Optionally, the connector 230 can also include a cap or cover 235 configured to close the opening at the proximal end 230b of the connector 230. In addition, the connector 230 can include a Y-port 232 in communication with the lumen 234 and the opening at the distal end 230a. The Y-port 232 can additionally have a cap or cover 236 configured to close the opening at the proximal end 232a of the Y-port. The Y-port can be configured to receive tubing or other suitable means for delivering enteral feeding fluid, medicine, or other fluids through the feeding tube 210.

The signal generator system 220 can be an electromagnetic field generator system, as shown in FIGS. 6-7, including a wire assembly 224 comprised of one or more electrical wires, for example two wires 224a and 224b as shown in FIG. 7. The electrical wires 224a and 224b can be made of copper or any other suitable material. The wires 224a and 224b can be twisted around each other along the length of the wire assembly 224. In one embodiment, as shown in FIG. 7, the wire assembly 224 can additionally include an elongated stiffener 224c twisted with the wires 224a and 224b to increase the rigidity of the wire assembly 224. The elongated stiffener 224c can be made of steel or any other suitable material. The twisted configuration of the wire assembly 224 can reduce any electromagnetic field surrounding the wires 224a and 224b along the twisted length of the wire assembly 224. This reduction is caused by the counteraction of the electromagnetic forces of the electrical wires 224a and 224b. Accordingly, the electromagnetic receiver 140 receives less, if any, signal interference from any electromagnetic fields generated by the wire assembly 224.

At a proximal end of the wire assembly 224, the electromagnetic field generator system 220 can include a connector 229. The connector 229 can operatively connect the system 200 to the control unit 130 of the display device 100. In one embodiment, the connector 229 can electrically connect the system 220 to the power source 150 of the display device 100. In another embodiment, the system 220 can include its own power source such as a battery 250.

In an embodiment of the invasive medical device assembly 200 that is in wireless communication with the display device 100, as shown in FIG. 4, the connector 229 can house a wireless chip 260 that is configured to communicate with a wireless chip 160 of the display device 100. In this embodiment, the invasive medical device assembly 200 can additionally include a control unit 230 including a memory 243 and a processor 232 to generate at least one drive signal for generating the electromagnetic field and transmitting a signal containing information about the at least one drive signal to the processor 132 of the display device 100.

As shown in FIGS. 6-7, at a distal end of the wire assembly 224, the wires form a coil configuration 222 forming coils thereby producing a magnetic field generator as described below. The coil 222 is formed from a plurality of spirals produced by wrapping a portion of the wires 224a and 224b around each other. As an electrical current is transmitted through the wires 224a and 224b, the current travels in a circular path defined by the coils. This circular motion of current produced an electromagnetic field, B field or electromagnetic radiation 226. Although the embodiment illustrated includes coils 222, it should be appreciated that the magnetic field generator 222 can include any alternate suitable mechanism or device which generates or produces magnetic energy, a magnetic field, or any other signal. In one embodiment, the magnetic field generator 222 includes a magnet such as a permanent magnet, resistive magnet or superconductive magnet.

In operation, when a power supply, e.g., power supply 150 or battery 250, sends electrical current to the coils 222, and the coils 222 transmit an electromagnetic field 226 capable of being detected by the electromagnetic receiver 140, the electromagnetic receiver 140 detects the electromagnetic field 226 generated by the magnetic field generator coils 222 inside the human body. The processor 132 causes the display device 100 to produce at least one representative image on one of the flexible electronic displays 110 or 120 which can assist a healthcare provider in a feeding tube placement procedure.

In an alternative embodiment (not shown), the signal generator system 220 can be incorporated directly into the invasive medical device 210, for example, by embedding the coil 222 and/or the wire assembly 224 into a wall 211 of a catheter 210.

When the in-scale display device 100 is used as part of a medical device position guidance system 10, the substrate 102 can be positioned on a subject in a predetermined arrangement such that the electromagnetic receiver 140 is in a predetermined position relative to the subject's anatomy. The predetermined position of the electromagnetic receiver 140 can be based on well-known external anatomical landmarks. The well-known external anatomical landmarks can be bony landmarks, as the bony landmarks can be located visually or palpated on subjects of any shape or size regardless of physical presentation of the subject, such as the presence of adipose tissue, edema, or other tissues. For example, as illustrated in FIG. 1, when the medical device position guidance system 10 is used to determine a subject's upper anatomy such as for inserting an enteral catheter (feeding tube), the signal receiver 140 of the display device 100 can be placed at the xiphoid process, which is the cartilaginous section at the lower end of the sternum which is generally positioned along the mid-sagittal line of the body. There may be other points of the body to which the predetermined arrangement of the display device 100 or the predetermined position of the signal receiver 140 could be reliably co-located or located with a predetermined offset for use in a reliable position guidance system.

The medical device position guidance system 10 can also be used in a method 1000 for guiding the placement of an invasive medical device, e.g., enteral feeding tube 210. The method 1000 includes a first step 1002 of providing the medical device position guidance system 10 as described above, e.g., the system 10 as illustrated in FIG. 3. In step 1004, the substrate 102 of the display device 100 is positioned on a surface of the subject's body 50. The substrate 102 can be fastened to the subject's body 50 or garment and attached to the subject's body 50 or garment with an attachment device to secure the positioning of the substrate 102. The substrate 102 can be positioned in a predetermined arrangement on the subject's body 50 based on bony landmarks of the subject's anatomy such that the signal receiver 140 of the display device 100 is in a predetermined position.

In step 1006, the signal system 200 is inserted into the feeding tube 210 such that the coil 222 is disposed at the distal end 212 of the feeding tube 210. Then, in step 1008, the feeding tube 210 can be inserted into the subject, e.g., through the subject's nose or mouth.

In step 1010, the processor 132 sends at least one drive signal to generate a signal 226 with the signal generator 222, e.g., coil. Once the feeding tube 210 has been inserted, a signal, e.g., the voltage of the current induced in the electromagnetic receiver 140 by an electromagnetic field 226, is detected in step 1012. In step 1014, the signal, e.g., the voltage of the induced current of the electromagnetic receiver 140, can be used by the processor 132 to determine the position and orientation of the coil 222 of the signal generator system 220.

In step 1016, the processor 132 then causes the first flexible electronic display 110 to display the position and orientation of the signal generator 222 within the distal end of the feeding tube 210 relative to the electromagnetic receiver 140 in a superior/inferior direction and/or a medial/lateral direction relative to the subject 50. The processor 132 also causes the second flexible electronic display 120 to display the position and orientation of the signal generator 222 within the distal end of the feeding tube 210 relative to the signal receiver 140 in a superior/inferior direction and a dorsal/ventral direction relative to the subject 50. The images displayed can be in the form of at least one reference image that is in-scale with the size and position of the subject's body 50.

Although the above embodiments relate to positioning an end of a feeding tube catheter, it should be appreciated that the display device of the medical device position guidance system is operable to assist in the placement of any medical device or invasive component into a mammal in the course of stent placement, ablation, blockage removal, heat treatment, surgical procedure, fluid delivery or any other suitable invasive procedure. It should be appreciated that any type of catheter may be used for any of the medical procedures described above. It should also be appreciated that any suitable invasive medical device can be used in place of a catheter. Further, it should be appreciated that the in-scale display device can be used to display a reference image of any other suitable subject outside the medical field when a sufficient signal generator is used with the in-scale display device.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A display device comprising:
    a first flexible electronic display screen and a second flexible electronic display screen;
    at least one signal receiver configured to detect a signal generated by a signal generator;
    a processor;
    a memory device storing instructions which, when executed by the processor, causes the processor to:
      (i) detect the signal generated by the signal generator,
      (ii) determine the distance between the at least one signal receiver and the signal generator, and
      (iii) cause the display device to display at least one reference image of a location of the signal generator on the at least one flexible electronic display screen in-scale with a subject's body when the signal generator is positioned below the display device; and a flexible substrate formed from a flexible material and comprising an attachment device configured to secure the display device to the subject;

wherein the first flexible electronic display screen and the second flexible electronic display screen are integrated into the flexible substrate; and wherein the second flexible electronic display screen is configured to be positioned generally perpendicular to the first flexible electronic display screen when the attachment device is secured to the subject's body.

2. The display device of claim 1, wherein the attachment device is configured to secure the display device to a garment worn by the subject.

3. The display device of claim 1, wherein the substrate comprises a flexible wrap.

4. The display device of claim 3, wherein the flexible wrap is configured to be adjustable in size based on a size of the subject's body.

5. The display device of claim 1, wherein the first flexible electronic display is configured to be positioned on an anterior or posterior surface of the subject's body and the second flexible electronic display is configured to be positioned on a lateral surface of the subject's body.

6. The display device of claim 3, wherein the flexible wrap includes an adjustable section positioned between the first flexible electronic display and the second flexible electronic display.

7. The display device of claim 1, wherein the first flexible electronic display screen is configured to display movement of the signal generator in the superior/inferior and lateral/medial directions of the subject's body.

8. The display device of claim 1, wherein the second flexible electronic display screen is configured to display movement of the signal generator in the superior/inferior and dorsal/ventral directions of the subject's body.

9. The display device of claim 1, wherein the first flexible electronic display screen comprises at least one flexible LED mat.

10. The display device of claim 1, wherein the signal receiver is an electromagnetic receiver, further wherein the signal generator is an electromagnetic field generator.

11. A medical device position guidance system comprising:
an invasive medical device assembly; and
a display device, the display device being positionable over a surface of a subject;
the invasive medical device assembly including a signal generator and an invasive medical device configured to support the signal generator, the invasive medical device having an end portion configured to be inserted into the subject;
the display device including:
a first flexible electronic display screen and a second flexible electronic display screen, wherein the first flexible electronic display is configured to be positioned on an anterior or posterior surface of the subject's body and the second flexible electronic display is configured to be positioned on a lateral surface of the subject's body;
at least one signal receiver configured to detect a signal generated by the signal generator of the invasive medical device assembly;
a processor; and
a memory device storing instructions which, when executed by the processor, cause the processor to
(i) detect the signal emitted by the signal generator,
(ii) determine the distance between the at least one signal receiver and the signal generator, and
(iv) cause the display device to display at least one reference image of the location of the signal generator on the at least one flexible electronic display screen in-scale with the subject's body when the invasive medical device assembly is positioned below the display device; and
a flexible substrate formed from a flexible material and comprising an attachment device configured to secure the display device to the subject;
wherein the first flexible electronic display screen is configured to display movement of the signal generator in the superior/inferior and lateral/medial directions of the subject's body, and the second flexible electronic display screen is configured to display movement of the signal generator in the superior/inferior and dorsal/ventral directions of the subject's body.

12. A method of guiding positioning of an invasive medical device within a subject's body, the method comprising the steps of:
providing a medical device position guidance system, the system including:
an invasive medical device assembly including a signal generator and an invasive medical device configured to support the signal generator, the invasive medical device having an end portion configured to be inserted into the subject's body; and
a display device including:
at least one flexible electronic display screen;
at least one signal receiver configured to detect a signal generated by the signal generator of the invasive medical device assembly;
a processor; and
a memory device storing instructions which, when executed by the processor, cause the processor to
(i) detect the signal generated by the signal generator,
(ii) determine a distance between the at least one signal receiver and the signal generator, and
(iii) cause the display device to display at least one reference image of a location of the signal generator on the at least one flexible electronic display screen in-scale with the subject's body when the invasive medical device assembly is positioned below the display device; and
a flexible substrate formed from a flexible material and comprising an attachment device configured to secure the display device to the subject;
positioning the display device on a surface of the subject's body in a predetermined arrangement such that the at least one signal receiver is in a predetermined position;
determining a position of the signal generator relative to the at least one signal receiver; and
displaying the position of the signal generator in-scale on the at least one flexible display when the signal generator passes an area of the subject covered by the display device;
wherein the at least one flexible electronic display screen includes a first flexible electronic display screen configured to display movement of the signal generator in-scale in the superior/inferior and lateral/medial directions of the subject's body and a second flexible electronic display screen configured to display movement of the signal generator in-scale in the superior/inferior and dorsal/ventral directions of the subject's body.

\* \* \* \* \*